United States Patent
Brock-Fisher et al.

(10) Patent No.: US 11,278,932 B2
(45) Date of Patent: Mar. 22, 2022

(54) CAPACITIVE MICRO-MACHINED ULTRASOUND TRANSDUCER CELL

(71) Applicant: KONINKLIJKE PHILIPS N.V., Eindhoven (NL)

(72) Inventors: George Anthony Brock-Fisher, Eindhoven (NL); Richard Edward Davidsen, Eindhoven (NL); Carl Dean Herickhoff, Eindhoven (NL); Bout Marcelis, Eindhoven (NL); Wojtek Sudol, Eindhoven (NL); Junho Song, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 796 days.

(21) Appl. No.: 14/914,019

(22) PCT Filed: Aug. 18, 2014

(86) PCT No.: PCT/EP2014/067521
§ 371 (c)(1),
(2) Date: Feb. 24, 2016

(87) PCT Pub. No.: WO2015/028325
PCT Pub. Date: Mar. 5, 2015

(65) Prior Publication Data
US 2016/0203809 A1      Jul. 14, 2016

Related U.S. Application Data

(60) Provisional application No. 61/871,926, filed on Aug. 30, 2013.

(30) Foreign Application Priority Data

Oct. 3, 2013   (EP) .................................. 13187232

(51) Int. Cl.
*B06B 1/02*    (2006.01)
*A61B 8/00*    (2006.01)
*G10K 11/00*   (2006.01)

(52) U.S. Cl.
CPC .......... *B06B 1/0292* (2013.01); *A61B 8/4494* (2013.01); *G10K 11/002* (2013.01)

(58) Field of Classification Search
None
See application file for complete search history.

(56) References Cited

U.S. PATENT DOCUMENTS 5,396,207 A    3/1995 Dorri et al.
5,488,957 A *  2/1996 Frey .......................... C09J 5/00
                                                  600/472

(Continued)

FOREIGN PATENT DOCUMENTS

EP     2540227 A1    1/2013
JP    03188830 A     8/1991

(Continued)

OTHER PUBLICATIONS

Zhuang et al., "Biocompatible coatings for CMUTs in a harsh, aqueous environment", Journal of Micromechanics and Microengineering, vol. 17, Apr. 17, 2007, pp. 994-1001. (Year: 2007).*

(Continued)

*Primary Examiner* — Katherine L Fernandez

(57) ABSTRACT

The invention relates to a capacitive micro-machined ultrasound transducer (CMUT) cell (6) comprising a cell floor (31) having a first electrode (7); a cell membrane (5) having a second electrode (7') which opposes the first electrode and vibrates during transmission or reception of acoustic energy; a transmitter/receiver coupled to the first and second electrodes which causes the cell membrane to vibrate at an acoustic frequency and/or receives signals at an acoustic frequency; and an acoustic lens (13), overlaying the cell (Continued)

membrane, and having an inner surface opposing the cell membrane and an outer, patient-facing surface. According to the present invention the acoustic lens comprises at least one layer of a material selected from the group of: polybudatiene, polyether block amide (PEBAX), polydimethylsiloxane (PDMS) and buthylrubber.

20 Claims, 8 Drawing Sheets

(56) References Cited

U.S. PATENT DOCUMENTS

| | | | |
|---|---|---|---|
| 5,708,360 A | 1/1998 | Yui | |
| 5,834,687 A | 11/1998 | Talbot | |
| 6,831,876 B1 | 12/2004 | Cartwright | |
| 8,801,615 B2 | 8/2014 | Lockwood | |
| 2002/0006079 A1* | 1/2002 | Saito | G10K 11/30 367/150 |
| 2004/0113524 A1 | 6/2004 | Baumgartner | |
| 2005/0075572 A1 | 4/2005 | Mills | |
| 2005/0146247 A1* | 7/2005 | Fisher | B06B 1/0292 310/334 |
| 2005/0165312 A1 | 7/2005 | Knowles | |
| 2005/0245829 A1* | 11/2005 | Wakabayashi | G10K 11/30 600/459 |
| 2006/0173344 A1 | 8/2006 | Marian | |
| 2008/0025145 A1 | 1/2008 | Peszynski | |
| 2008/0156577 A1 | 7/2008 | Dietz et al. | |
| 2008/0214938 A1 | 9/2008 | Solomon et al. | |
| 2010/0290318 A1 | 11/2010 | Stein et al. | |
| 2012/0010538 A1* | 1/2012 | Dirksen | A61B 8/00 601/2 |
| 2012/0320710 A1 | 12/2012 | Sato et al. | |
| 2013/0109950 A1* | 5/2013 | Herzog | A61B 8/0825 600/407 |
| 2013/0301394 A1* | 11/2013 | Chen | B06B 1/0292 367/155 |
| 2014/0005706 A1* | 1/2014 | Gelfand | A61N 7/022 606/169 |
| 2014/0112107 A1* | 4/2014 | Guo | B06B 1/00 367/191 |
| 2014/0125193 A1* | 5/2014 | Chowdhury | B06B 1/0292 310/300 |
| 2014/0204717 A1* | 7/2014 | Kunkel | G10K 11/18 367/137 |
| 2014/0265721 A1* | 9/2014 | Robinson | B06B 1/0292 310/300 |
| 2014/0292147 A1* | 10/2014 | Kim | H01L 41/0825 310/327 |

FOREIGN PATENT DOCUMENTS

| | | |
|---|---|---|
| JP | 2004337240 A | 12/2004 |
| JP | 2007301295 A | 11/2007 |
| JP | 2009213785 A | 9/2009 |
| WO | 2006121765 A2 | 11/2006 |
| WO | 2008135896 A1 | 11/2008 |
| WO | 2010038162 A1 | 4/2010 |

OTHER PUBLICATIONS

Hou et al "An Integrated Optoacoustic Transducer Combining Etalon and Black PDMS Structures" IEEE Trans Ultrason Ferroelectr. Freq. Control Dec. 2008; 55(120 p. 2719-2725.

Song et al Large Improvement of the Electrical Impedance of Imaging and High-Intensity Focused Ultrasound . . . IEEE Trans. on Ultrasonics, Ferroelectrics, and Frequency Control., vol. 59, No. 7 Jul. 2012.

Li, "Surface Modification Technique for Acoustic Chemical Sensor Arrays based on CMUTS" Dissertation der Martin-Luther Universitat Halle-Wittenberg, Dec. 5, 1982.

* cited by examiner

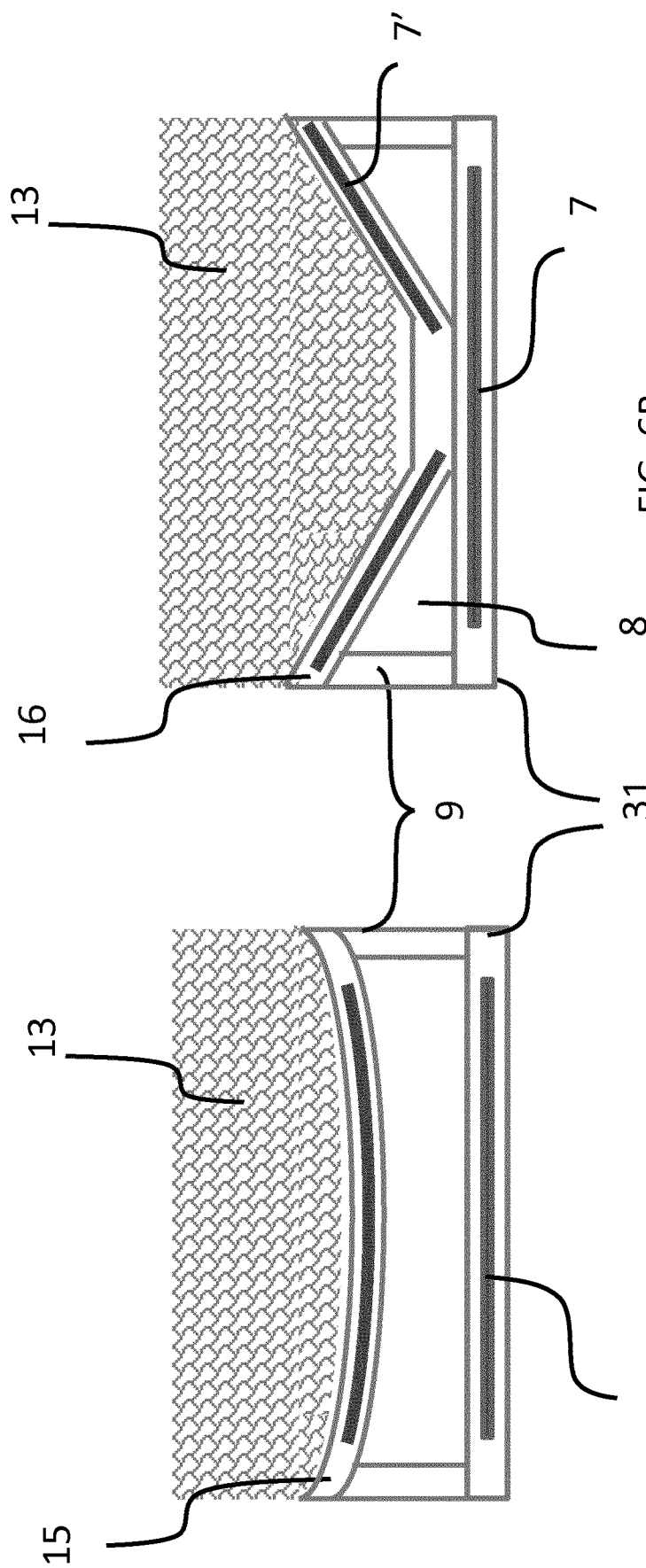

CAPACITIVE MICRO-MACHINED ULTRASOUND TRANSDUCER CELL

This application is the U.S. National Phase application under 35 U.S.C. § 371 of International Application No. PCT/EP2014/067521, filed on Aug. 18, 2014, which claims the benefit of EP Application No. 13187232.7 filed Oct. 3, 2013 and U.S. Provisional Application 61/871,926 filed Aug. 30, 2013. These applications are hereby incorporated by reference herein.

FIELD OF THE INVENTION

The invention relates to a capacitive micro-machined ultrasound transducer (CMUT) cell comprising a cell floor having a first electrode; a cell membrane having a second electrode which opposes the first electrode and vibrates during transmission or reception of acoustic energy; a transmitter/receiver coupled to the first and second electrodes which causes the cell membrane to vibrate at an acoustic frequency and/or receives signals at an acoustic frequency; and an acoustic lens, overlaying the cell membrane, and having an inner surface opposing the cell membrane and an outer, patient-facing surface.

The invention further relates to an ultrasonic imaging system comprising such a cell.

BACKGROUND OF THE INVENTION

Central to any ultrasound (imaging) system is the ultrasound transducer which converts electrical energy in acoustic energy and back. Recent progress in semiconductor technology resulted in the development of capacitive micro-machined ultrasound transducers (CMUT). These transducers are considered to be potential candidates to replace the conventional piezoelectric based ultrasound transducers (PZT). A CMUT transducer cell comprises a cavity with a movable mechanical part also called a membrane and a pair of electrodes separated by the cavity. When receiving ultrasound waves, ultrasound waves cause the membrane to move or vibrate and the change the capacitance between the electrodes which can be detected. Thereby the ultrasound waves are transformed into a corresponding electrical signal. Conversely, an electrical signal applied to the electrodes causes the membrane to move or vibrate, thereby transmitting ultrasound waves.

Advantages of CMUTs are that they can be made using semiconductor fabrication processes and, therefore, may be easier integrated with application-specific integrated circuitry (ASIC); CMUT transducers offer low cost, extended frequency range, and finer acoustic pitch over traditional PZTs.

A CMUT transducer cell is known from US2012/0320710 A1; the cell is schematically illustrated in FIG. 1. The known CMUT cell contains a backing layer 12 that is located at the back side of the transducer 11 in relation to position of the investigated object (body), i.e. at the opposite side to the desired direction of the ultrasound wave propagation. The backing layer 12 is formed of a material that has substantially the same acoustic impedance as that of an acoustic lens 14 located at the front side of the CMUT 11, i.e. direction of the ultrasound wave propagation. The reason why the backing layer 12 is formed of a material with substantially the same acoustic impedance as the acoustic lens 14 is the following. The amount of change in acoustic impedance is the same in the front and back side directions. Therefore, acoustic energy of reflected waves at the CMUT interfaces is distributed at the same rate in these two directions. This results in the suppressing of the occurrence of multiple reflections caused at the interface of the transducer and the backing layer. In order to solve the multi reflection problem US2012/0320710 A1 suggest applying silicon rubber as a material for the acoustic lens.

US 2005/075572 A1 describes a micromachined ultrasonic transducer array that focuses in the elevation direction. A curved lens is used to narrow the beam width in the elevation direction so that contrast resolution is improved and clinically relevant. A representative lens materials include silicon rubbers like GE RTV60, RTV 560 and RTV 630.

A drawback of the known CMUT transducer cell is that interactions between the CMUT membranes and the material of the lens 14 may reduce the acoustic performance of the transducer.

SUMMARY OF THE INVENTION

It is an object of the present invention to provide a capacitive micro-machined ultrasound transducer cell of the kind set forth in the opening paragraph which provides an improved acoustic wave propagation.

This object is achieved according to the invention by providing a CMUT cell wherein an acoustic lens comprises at least one layer of a material selected from the group of: polybudatiene, polyether block amide (PEBAX), polydimethylsiloxane (PDMS) and buthylrubber.

This group of materials: polyether block amide (PEBAX), polydimethylsiloxane (PDMS), buthylrubber and polybudatiene provides an acousticalcouplling of the lens to the membrane of the cell. These materials exhibit an acoustic loss per millimeter for acoustic energy passing therethrough of less than 1.5 dB for energy of an acoustic frequency of 2 MHz and further exhibits an acoustic propagation velocity for acoustic energy passing therethrough which is in the range of 0.5 to 2.5 mm/microsecond.

While the choice of the commonly used lens materials for the ultrasound transducers is mainly defined by the requirements of PZT based ultrasound system such as Room Temperature Vulcanizing silicon (RTV), which is a type of silicon rubber. The CMUTs, due to the different process of the conversion of electrical energy, in acoustic energy have different requirements to the materials that may be used for acoustic lenses of CMUT transducers. The acoustic lens, which may have focusing or acoustic window properties, shall fulfill specific requirements to the range of acoustic loss and acoustic propagation velocity for acoustic energy. As an example, for the optimal operation, the PZTs require a lens with an additional "matching" layer that is aimed to solve the problem of an impedance mismatch between the PZT with the impedance of around 30 MRayls and a typical propagation medium, such as water or soft tissue with the impedance of 1.6 MRayls. Unlike PZTs, CMUTs acoustic impedance is close to or lower than that of tissue with the result that a CMUT based ultrasound transducer will require a different type of matching layer from PZT transducers.

It was discovered that common traditional RTV acoustic lens materials, a room temperature curing rubber which is easily cast in place and formed by molding into a desired shape, introduces an additional acoustic loss mechanism in addition to normal frequency dependent attenuation. This loss is manifested in increased attenuation on the order of 2 dB and a downshift in center frequency of up to 4 MHz.

The choice of materials according to the invention, i.e. materials that exhibit an acoustic loss per millimeter for acoustic energy passing therethrough of less than 1.5 dB for energy of an acoustic frequency of 2 MHz and further exhibit an acoustic propagation velocity for acoustic energy passing therethrough which is in the range of 0.5 to 2.5 mm/microsecond, provides a superior coupling and propagation of the acoustic energy from the CMUT into the propagation medium. Compared to traditional RTV acoustic materials a minimal attenuation and frequency downshift are observed. The acoustical coupling of the acoustic lens to the membrane of the CMUT provides an optimal preservation of mechanical properties of the vibrating (moving) part and results in the optimal acoustic energy propagation.

In another embodiment of the present invention the acoustic lens further comprises at least one layer of liquid.

Material considered being a liquid if it has viscosity up to 200000 centipoise.

In another embodiment of the present invention the acoustic lens further comprises at least one layer of gel.

A gel is considered to be a dispersion of molecules of a liquid, discontinuous phase within a solid, continuous phase a dilute, three-dimensional network of cross-linked polymer molecules which exhibit no flow when in the steady-state.

The liquid and gel materials may exhibit an acoustic loss per millimeter for acoustic energy passing therethrough of less than 1.5 dB for energy of an acoustic frequency of 2 MHz and further exhibits an acoustic propagation velocity for acoustic energy passing therethrough which is in the range of 0.5 to 2.5 mm/microsecond. Their application as one of the additional layers of the acoustic lens provides an improved coupling and transfer of the acoustic energy from the transducer into the propagation medium (tissue, body, etc).

In another embodiment of the present invention the acoustic lens of the CMUT cell further comprises at least one of the following layers: (i) a layer of moisture barrier; (ii) a layer of adhesive material; (iii) a layer of conductive material arranged to act as a radio frequency shield; (iv) an acoustic wave focusing layer; (v) a durable exterior layer located as the outer surface.

The layer of moisture barrier will provide a moisture protection, and the layer of conductive material may be adapted to act as a radio frequency (RF) shield. Essentially, the acoustic wave focusing layer provides desired focusing means for the acoustic wave propagation; and the durable exterior layer located as the outer patient-facing surface can provide a wear resistance, resistance to solvents or disinfectant solutions. The thickness of these layers shall be kept as low as possible, for example below 20 micrometer, for preserving the acoustic coupling of the elastomer, or liquid, or gel layers to the membrane of the CMUT cell.

In an embodiment of the present invention the liquid is one of: water and uncured PDMS.

In an embodiment of the present invention the gel is a silicone gel.

Water and silicone gel possess critical stiffness and attenuation properties that cause minimal attenuation and frequency downshift of the propagated acoustic wave.

Yet, in another embodiment of the present invention the acoustic lens further comprises a moisture barrier that is one of: polyimide, mylar, polyethylene or parylene.

Yet, in another embodiment of the present invention the acoustic lens further comprises a durable exterior layer located as the outer surface and that is one of polyimide or polyethylene.

Yet, in another embodiment of the present invention the acoustic lens further comprises an adhesive material that is silicon oxide.

These and other aspects of the invention will be apparent from and elucidated with reference to the embodiments described hereinafter.

BRIEF DESCRIPTION OF THE DRAWINGS

In the drawings:

FIG. 6A shows schematically and exemplarily a side view of the CMUT cell.

FIG. 6B shows schematically and exemplarily side view of the CMUT cell wherein the membrane is a collapsed membrane;

DETAILED DESCRIPTION OF EMBODIMENTS

Figure 1:
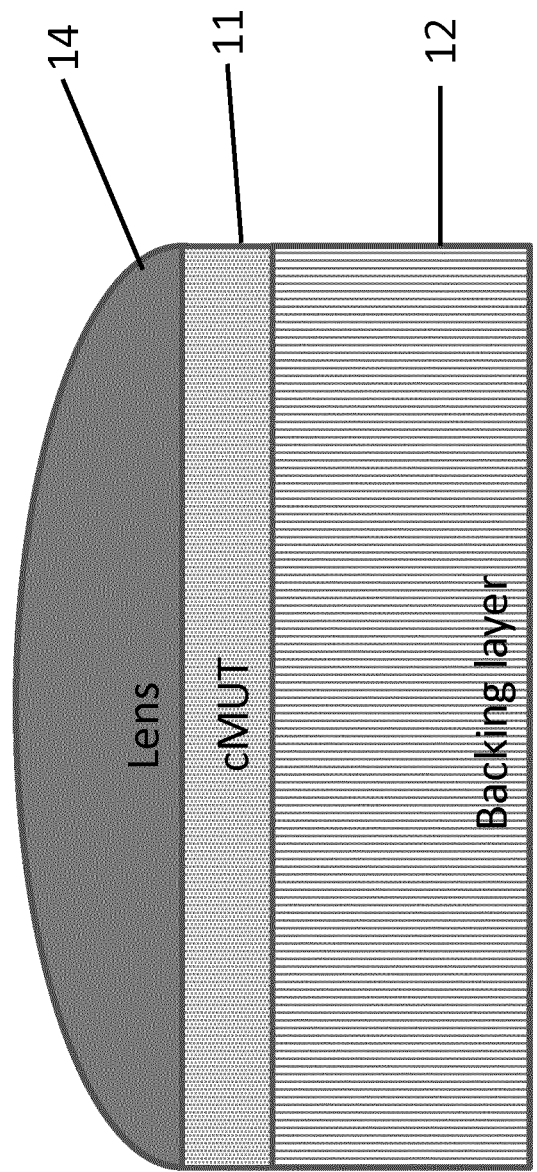
FIG. 1 shows schematically and exemplarily a side view of a CMUT cell of the prior art.
Figure 2:
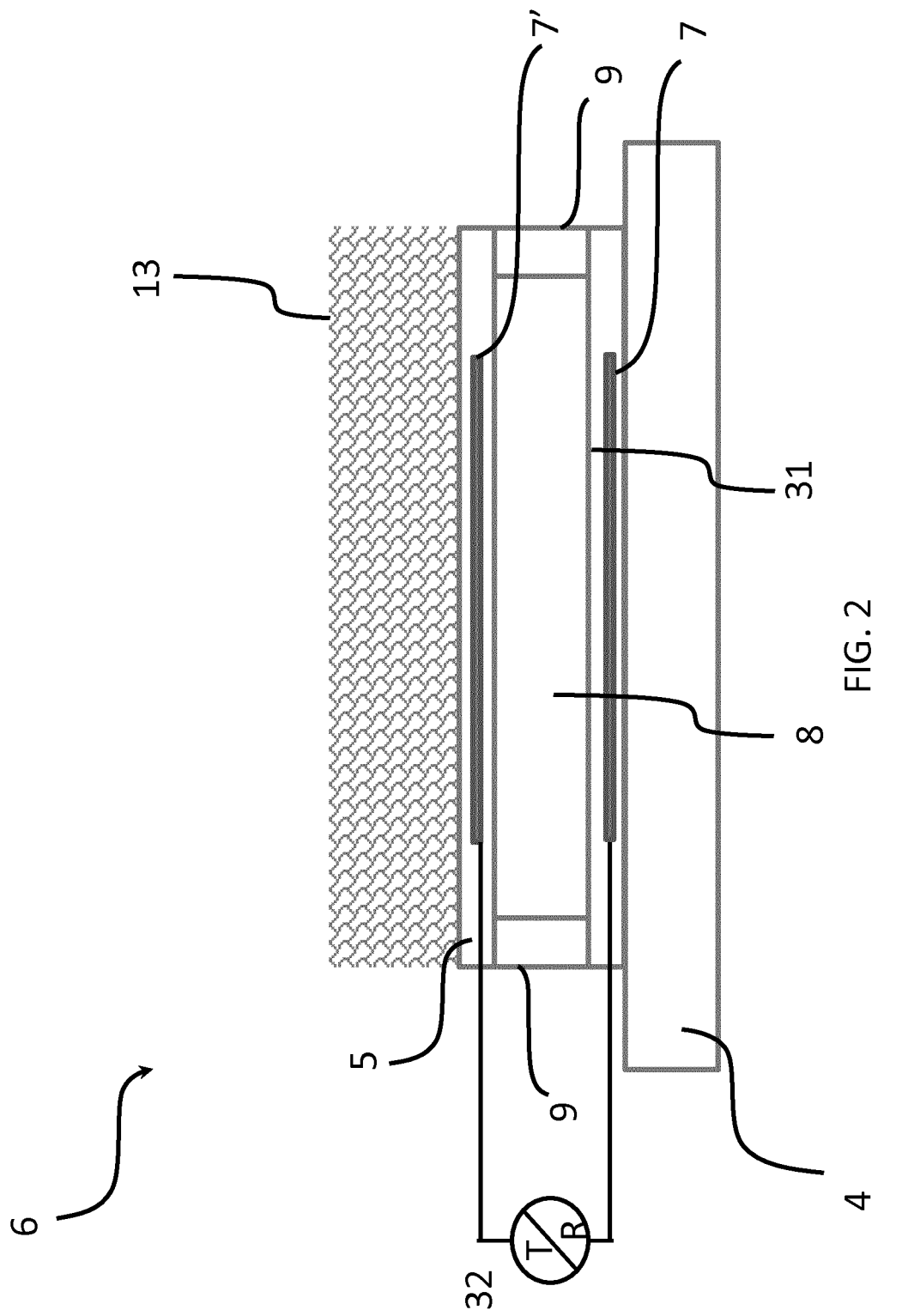
FIG. 2 shows schematically and exemplarily a side view of a CMUT cell comprising acoustic lens according to the present invention.

FIG. 2 shows schematically and exemplarily a CMUT cell in cross section according to the present invention. Such CMUT cell is typically fabricated on a substrate 4, such as a silicon wafer. The CMUT transducer of the ultrasound system may comprise one or more CMUT cells 6. The CMUT cells may be either individually activated or in combination with each other. The individual cells can have round, rectangular, hexagon or other peripheral shapes.

Each CMUT cell has at least a pair of electrodes 7' and 7 separated by a cavity 8. The cavity 8 is formed in between a membrane 5 that is suspended over a cell floor 31. The membrane 5 may be made of silicon nitride and is adapted to move or vibrate. It can be suspended over the cell floor 31 through a plurality of supporting portions 9 (in FIG. 2 two supporting portions 9 are shown). The electrodes 7, 7' are made of electrically conductive material, such as metal. The bottom electrodes 7 may be embedded in the floor of the cell 31, while the top electrode 7' may be embedded in the membrane 5. The electrode 7 and 7' may be also deposited on the cell floor 31 or the membrane 5 as additional layers. The bottom electrode 7 is typically insulated on its cavity-facing surface with an additional layer (not pictured). A preferred insulating layer is an oxide-nitride-oxide (ONO) dielectric layer formed above the bottom electrode 7 and below the membrane electrode 7'. The ONO-dielectric layer advantageously reduces charge accumulation on the electrodes which leads to device instability and drift and reduction in acoustic output pressure. The supporting portions 9 may be made of an insulating material such as silicon oxide or silicon nitride. The cavity 8 can be either air- or gas-filled, or wholly or partially evacuated. Two electrodes 7 and 7' separated by the cavity 8 represent a capacitance. An application of electrical signal through a transmitter/receiver 32 coupled to the electrodes 7 and 7' causes a mechanical movement/vibration of the membrane 5, which results in the change of the capacitance and can be manipulated by the associated with the CMUT transducer electronics.

According to the principles of the present invention, the membrane 5 of the CMUT cell is acoustically coupled to an acoustic lens 13 overlaying the cell membrane, and having an inner surface opposing the cell membrane and an outer surface located in the opposite direction of the inner surface. The outer surface may be either a patient or an object facing side, which can be the subjects of the untrasound examination. The distinguishing feature of the current invention is that the acoustic lens 13 comprises at least one layer of a material selected from the group of: polybudatiene, polyether block amide (PEBAX), polydimethylsiloxane (PDMS) and buthylrubber. These materials are elastomers (material considered being an elastomer if it has stiffness in the range from 20 up to 60 durometer), which exhibit an acoustic loss per millimeter for acoustic energy passing therethrough of less than 1.5 dB for energy of an acoustic frequency of 2 MHz and the lens further exhibits an acoustic propagation velocity for acoustic energy passing therethrough which is in the range of 0.5 to 2.5 mm/microsecond. The acoustic lens 13 shall be understood as having either focusing or an acoustic window (none-focusing means) properties.

These specific materials that can be comprised in the lens provide optimal conditions for the acoustic wave propagation, wherein the optimal conditions are defined by the specific CMUT process of the conversion of electrical energy in acoustic energy.

The lens material property of the acoustic propagation velocity (v) for acoustic energy can be also expressed in acoustic impedance (Z). The acoustic impedance of a material is defined as the product of its density (p) and acoustic velocity: $Z=p*v$. Therefore, the provided advantages of applying either polyether block amide (PEBAX), or polydimethyl-siloxane (PDMS), or buthylrubber, or polybudatiene as a lens layer may be also expressed as the acoustic lens 13 which exhibits an acoustic loss per millimeter for acoustic energy passing therethrough of less than 1.5 dB for energy of an acoustic frequency of 2 MHz and the lens further exhibits an acoustic impedance for acoustic energy passing therethrough which is in the range of 0.5 to 2.0 MRayl.

In another embodiment of the present invention the acoustic lens 13 comprises at least one layer selected from the group of materials: polyether block amide (PEBAX), polydimethylsiloxane (PDMS), buthylrubber and polybudatiene layers that is preferably in contact with (overlaying) the membrane 13. Elastomer materials, such as polyether block amide (PEBAX), cured polydimethylsiloxane (PDMS), buthylrubber and polybudatiene, fullfill the requirement of providing the acoustic loss per millimeter for acoustic energy passing therethrough of less than 1.5 dB for energy of an acoustic frequency of 2 MHz and the acoustic propagation velocity for acoustic energy passing therethrough which is in the range of 0.5 to 2.5 mm/microsecond. An application of at least one layer of elastomer in the acoustic lens 13 may provide minimum attenuation and frequency downshift of the acoustic signal within a broad bandwidth of CMUT transducers.

Figure 3:
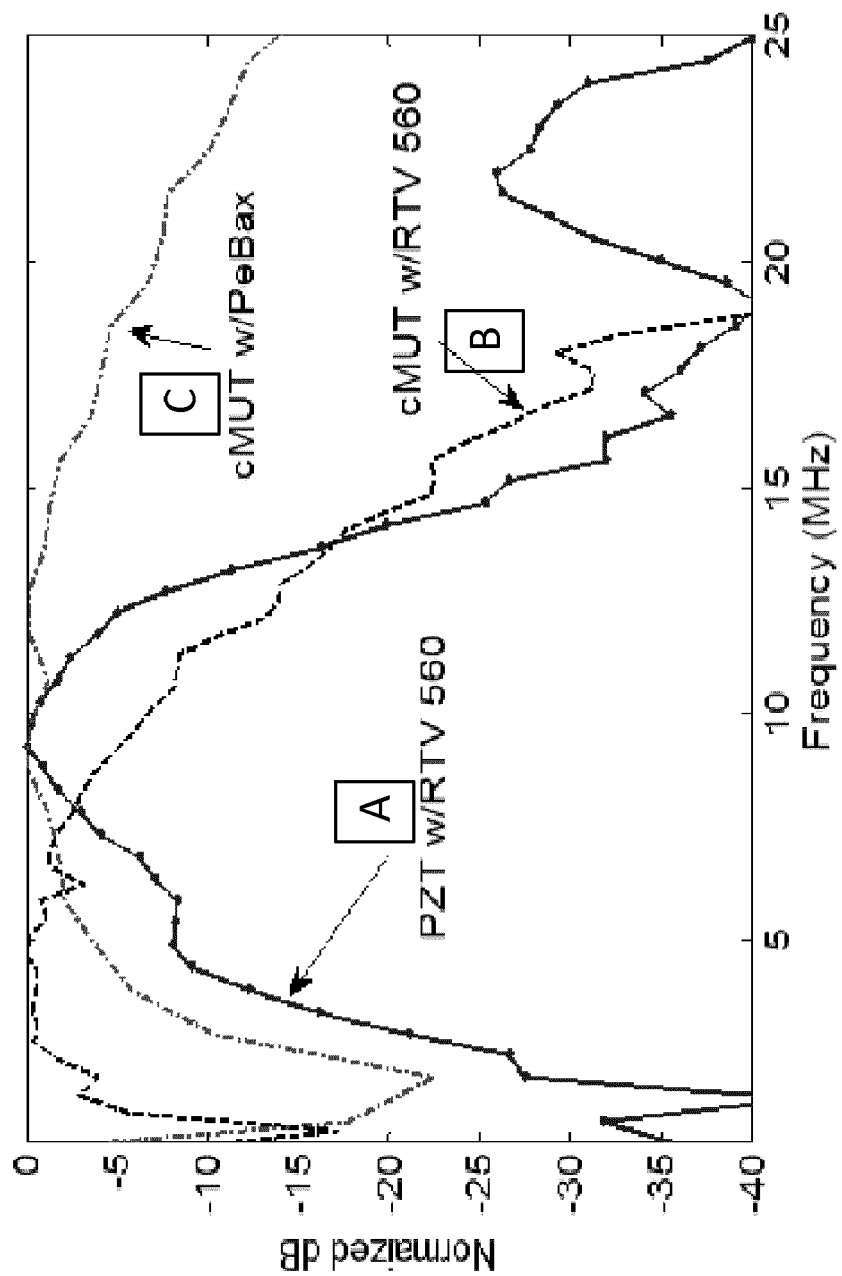
FIG. 3 is a graph showing an impulse response of three ultrasound transducers to illustrate the impact of the acoustic lens on a CMUT cell.

This is illustrated in FIG. 3. The figure shows a graph of a single impulse response of three ultrasound transducers within a given range of frequencies.

PZT coated with RTV560 (circles)—a standard PZT transducer array overlaid (applied) with a traditional RTV lens material and having a relatively narrow bandwidth centered at 9 MHz.

CMUT coated with RTV 560 (dashed line)—the same lens material as above (A) but applied on a CMUT transducer with the same aperture dimensions. The 8 MHz cMUT spectrum has been significantly downshifted with a center frequency around 4 MHz.

CMUT coated with PEBAX (dash and dotted line)—the same 8 MHz CMUT array as above (B), however, overlaid with the elastomer PEBAX material. The center frequency shows little to no downshift and the bandwidth is quite large, far exceeding the PZT equivalents. This illustrates the advantage of using the elastomer material such as PEBAX as an acoustic lens material.

One of polyether block amide (PEBAX), polydimethylsiloxane (PDMS), buthylrubber and polybudatiene layers may be applied to the CMUT cell in accordance to the known fabrication processes, for example, spin coating, dip coating, spray coating, over molding, vacuum deposition.

In another embodiment of the present invention the acoustic lens 13 further comprises at least one layer of liquid that is preferably in contact with the membrane 13. An example of liquid materials may be water or uncured polydimethylsiloxane (PDMS). Yet, in another embodiment of the present invention the acoustic lens 13 comprises at least one layer of gel, for example, silicone gel.

In order to combine the acoustic wave propagation benefits provided by the acoustic lens 13, such as low attenuation and low frequency downshift, together with other properties that may be required in the ultrasound transducer operation (biocompatibility, abrasion resistance, etc.), additional material layers may be included in the acoustic lens 13. Conventional methods of the materials deposition can be applied, such as chemical vapor depositions, ion sputtering, electron beam deposition, spin coating, etc.

Figure 4:
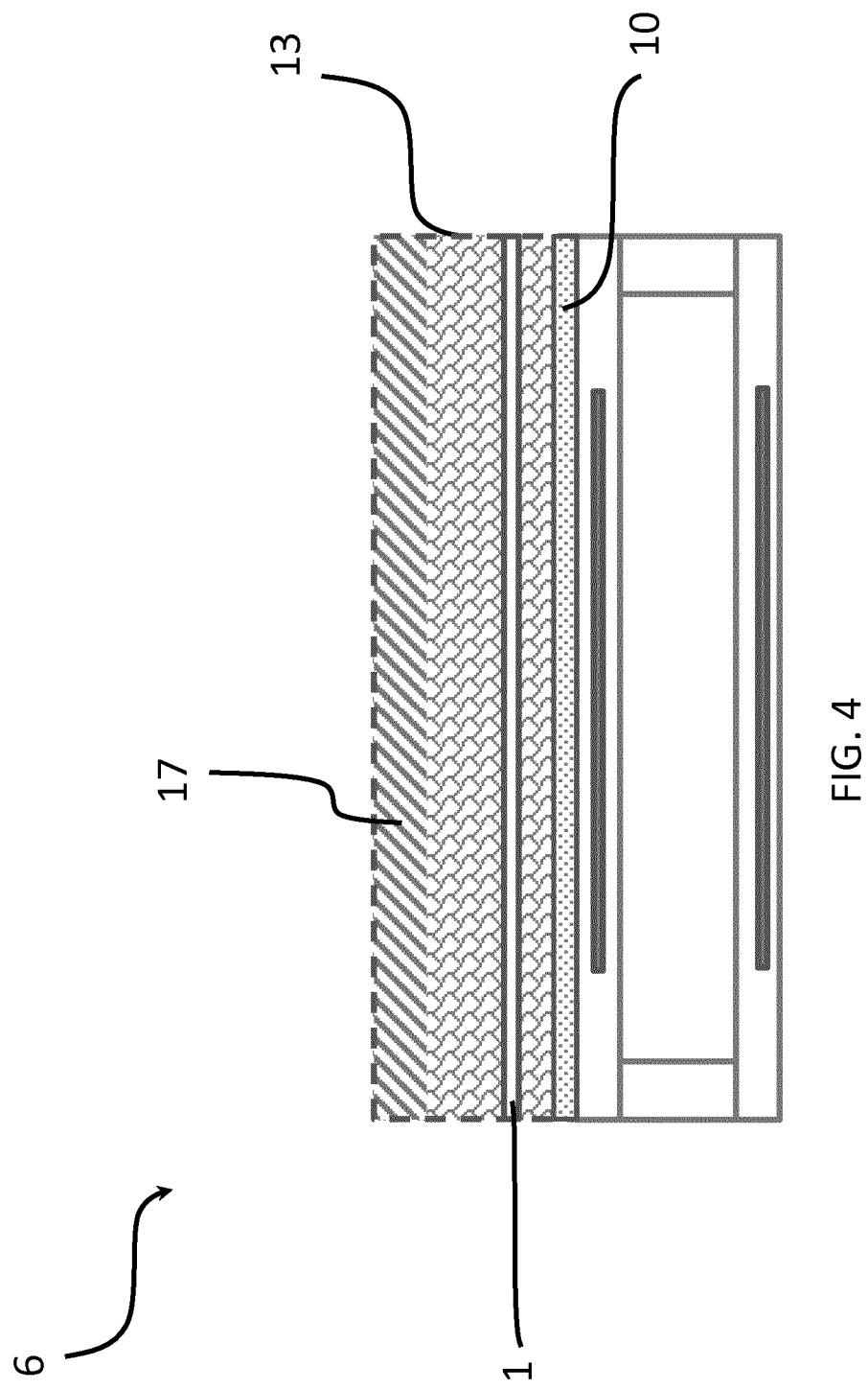
FIG. 4 shows schematically and exemplarily side view of the CMUT cell comprising additional layers included in the acoustic lens.

A schematic representation of the further embodiment of the present invention is shown in FIG. 4. In order to make the CMUT transducer 6 water proof a thin moisture barrier layer 10, for example polyimide, mylar, polyethylene or parylene, may be included in the lens 13. In preferred embodiment the moisture barrier layer may be applied on the outer surface (opposing the cavity side) of the membrane 5. For the electrical isolation or radio frequency shielding of the CMUT transducer a layer of conductive material 1, such as metal, may be included in the acoustic lens 13. To make the CMUT transducer 6 biocompatible a layer of biocompatible material may be applied (deposited) as the outer layer 17 of the lens 13. In order to assure the stability and acoustic conductivity of the acoustic lens 13, additional adhesive materials can be included therein for improvement of the bonding in between the layers of the lens 13. In preferred embodiment a thin layer of silicon oxide may be deposited in contact with the membrane 5 of the transducer 6. Silicon oxide of a thickness below 0.5 micrometer provides an improved adhesion of the acoustic lens 13 to the silicon nitride material commonly used for mechanical part of the CMUTs.

A step of the metal deposition may be also combined with the etching techniques (dry or wet etching) wherein, the metal layer may be used as an etch mask in order to open surface of bondpads areas in the CMUT cells' array. This allows providing an RF shield and electrical interconnects for the entire CMUT array.

A durable exterior layer located as the outer, patient-facing surface, may address other mechanical characteristics of the lens 13. For example, depending on the purpose of the ultrasound transducer, the following layers may be introduced in the lens: materials of different to elastomer abrasion resistance such as polyimide or polyethylene; material with different friction coefficients.

In addition to the elastomer (liquid and/or gel) layers the lens 13 may comprise a focusing material, RTV for example, that provides focusing of the acoustic wave into a desired focal point.

It is essential to note that the order of the additionally introduced layers into the lens 13 is not limited to the disclosed embodiments. One of the important requirements to the acoustic lens 13, which shall exhibit the acoustic loss per millimeter for acoustic energy passing therethrough of less than 1.5 dB for energy of an acoustic frequency of 2 MHz and the acoustic propagation velocity for acoustic energy passing therethrough which is in the range of 0.5 to 2.5 mm/microsecond, is that the additionally introduced layers preserve acoustic coupling of the membrane 5 of the CMUT transducer 6 to the acoustic lens, such as minimum attenuation and low shift of frequencies can be observed in the performance of the transducer.

In the case of the additional layers being included in the acoustic lens 13 and being applied in between the membrane 5 of the CMUT and either layer of the elastomer, liquid or gel, the acoustical coupling of membrane 5 and the elastomer can be achieved by thinning down the thicknesses of these additional layers. In the preferred embodiment the thickness of the additional layers may be below 5 micrometer.

As an example, the layer of parylene that may be applied to the outer surface of the membrane 5 (opposing the cavity side) as a moisture barrier may be 5 micrometer thick for the optimal acoustic wave propagation at the frequency of 7 MHz.

In another embodiment of the present invention the acoustic lens 13 of the CMUT transducer 6 comprises a layer of parylene that overlays the membrane 5; a layer of buthylrubber that overlays the parylene layer; followed by an overlaying metal layer that can be arranged to act as a radio frequency shield. Further an elastomer layer, which is at least one of PEBAX, PDMS, polybudatiene, overlays the metal layer and located at the outer patient-facing surface of the lens 13. The desired acoustic properties of the acoustic lens 13, according to the principles of the present invention, can be achieved with following layer thickness': for the acoustic wave with frequency of 7 MHz the combined thickness of the parylene and the buthylrubber layers is 5 micrometer and the thickness of the metal layer is lower than 0.2 micrometer.

Figure 5:
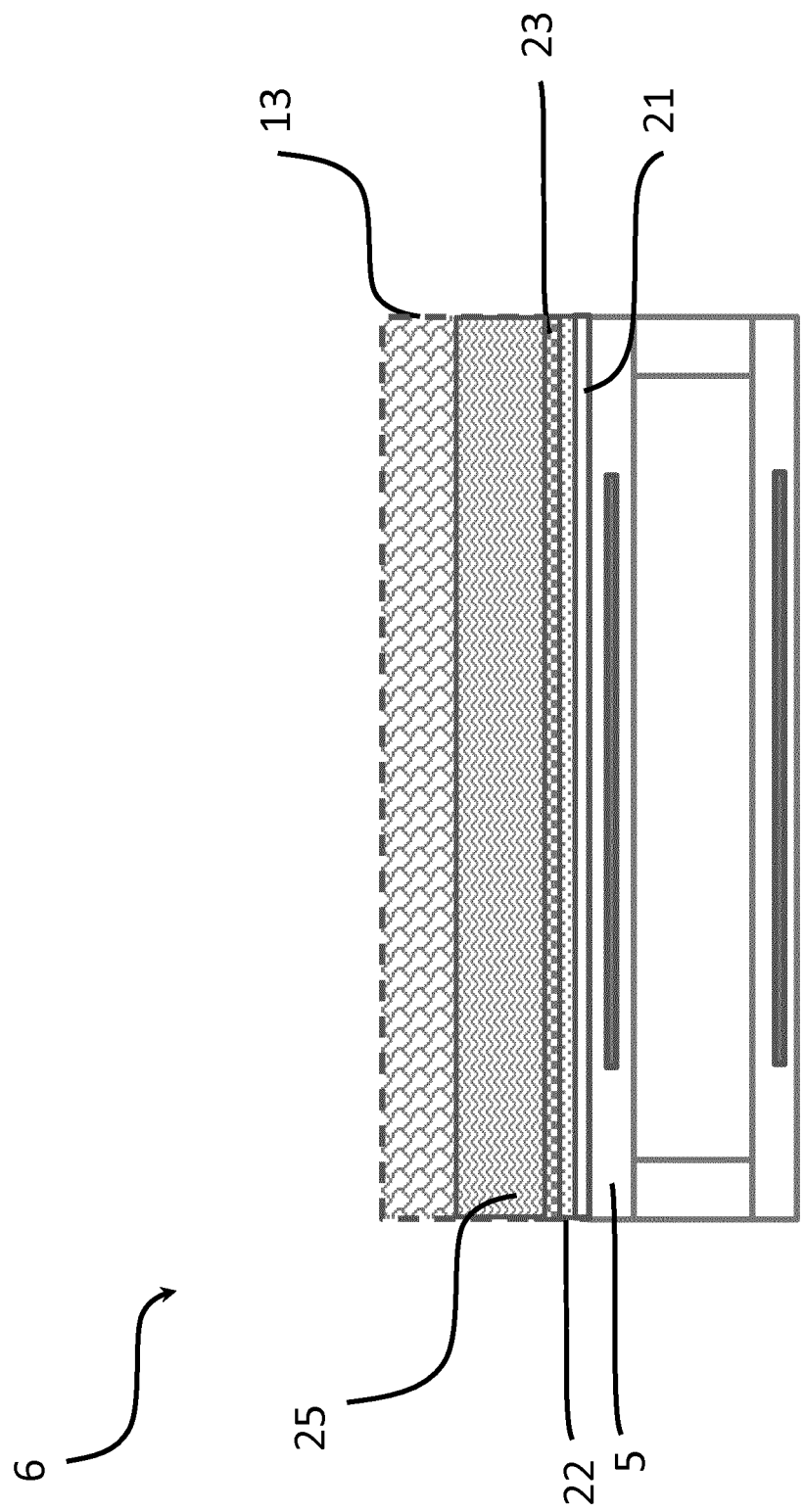
FIG. 5 shows schematically and exemplarily side view of the CMUT cell comprising additional layers included in the acoustic lens according to another embodiment of the present invention.

In another embodiment of the present invention is schematically represented in FIG. 5. The acoustic lens 13 of the CMUT transducer 6 comprises a layer of a metal 21 that overlays the membrane 5 and is adapted to act as radio frequency shield; a layer of parylene 22 overlaying the metal layer 21; then a buthylrubber layer 23 overlaying the parylene layer 22; followed by a layer of liquid 25 overlaying the buthylrubber layer 23 and the elastomer layer, which is at least one of PEBAX, PDMS, polybudatiene, overlaying the liquid layer and deposited at the outer patient-facing surface of the lens 13.

In this embodiment the parylene and buthylrubber layers act as moisture barriers for the CMUT surface against the water layer. In order to preserve the acoustic coupling of the elastomer to the membrane 5 the thicknesses of the additional layers can be kept the same as in the previous embodiment. The liquid layer thickness may be below 20 micrometer.

Yet in another embodiment of the present invention the acoustic lens 13 comprises either cured or uncured PDMS overlaying the CMUT membrane 5; a moisture barrier and conductive layers overlaying PDMS, followed by an elastomer material, such as PEBAX, applied as the outer patient-facing surface of the lens 13. Other additional layers with specified desired properties may be added on top of PEBAX layer in this embodiment as well.

In order to improve electromechanically coefficient of the CMUT cell different types of membrane designs may be used.

Referring to FIG. 6A, that shows schematically and exemplarily another embodiment of the present invention, the membrane 5 of the CMUT cell 6 is a "conventional" membrane 15 that can be adapted to vibrate under applied electrical signal or under received acoustic ways. The CMUT cell comprising the membrane 15 may be fabricated using known fabrication methods which can, for example, comprise deposition of a sacrificial layer steps, a deposition step of the membrane material, a step of dry or wet etching of the sacrificial material; followed by a step of sealing the cavity.

FIG. 6B shows yet another embodiment of the present invention, wherein the membrane 5 of the CMUT cell 6 is a collapsed membrane 16. The collapsed membrane 16 during the CMUT operation may be made collapsed relative to the cell floor 31 and the suspended portions of the membrane, which are in contact with the supporting portions 9, can be adapted to move/vibrate under applied electrical signal in between electrodes 7. From technology point of view, the CMUT with collapsed membrane can in principle be manufactured in any conventional way, comprising providing a CMUT with a membrane and applying different means, such as electrical (bias voltage) or pressure, in order to bring the membrane to a collapsed state.

Figure 6C:
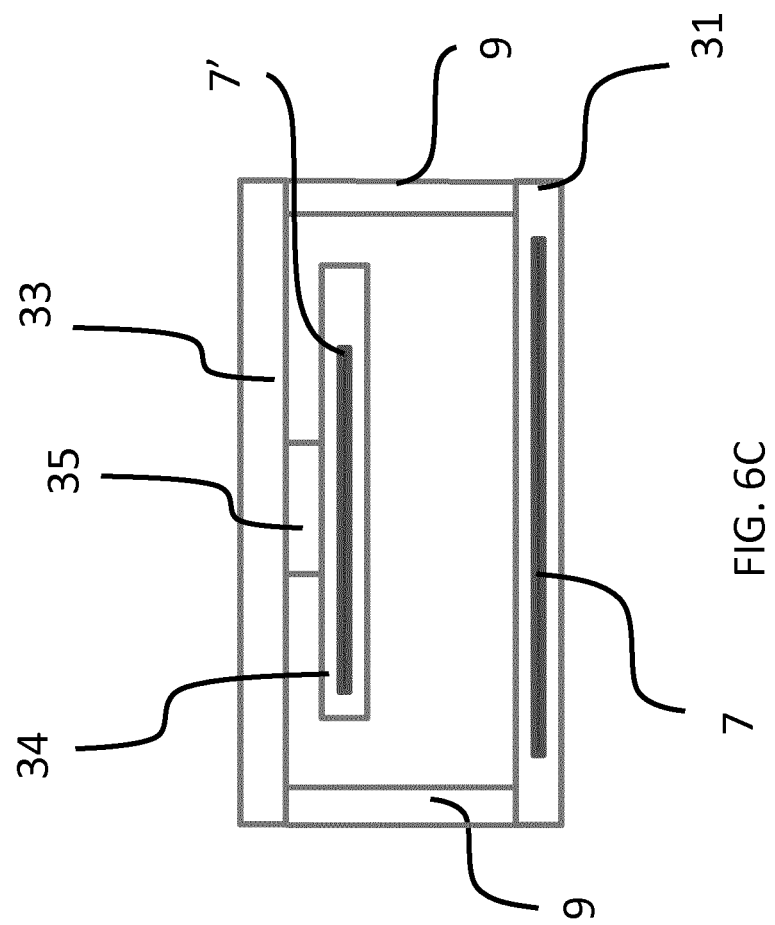
FIG. 6C shows schematically and exemplarily side view of the CMUT cell wherein the membrane is a "spring" membrane.

FIG. 6C shows yet another embodiment of the present invention, wherein the membrane 5 of the CMUT cellr 6 is a "spring" membrane. The "spring" membrane comprises a spring layer 33 supported by the supporting portions 9 and a mass layer 34. The mass layer 34 comprises the top electrode 7' and is coupled to the spring layer through the connector 35. In this design the spring layer 33 comprises a flexible material which permits the layer to vibrate during the CMUT operation, while the mass layer 34 preferably remains parallel to the cell floor 31.

Figure 7:
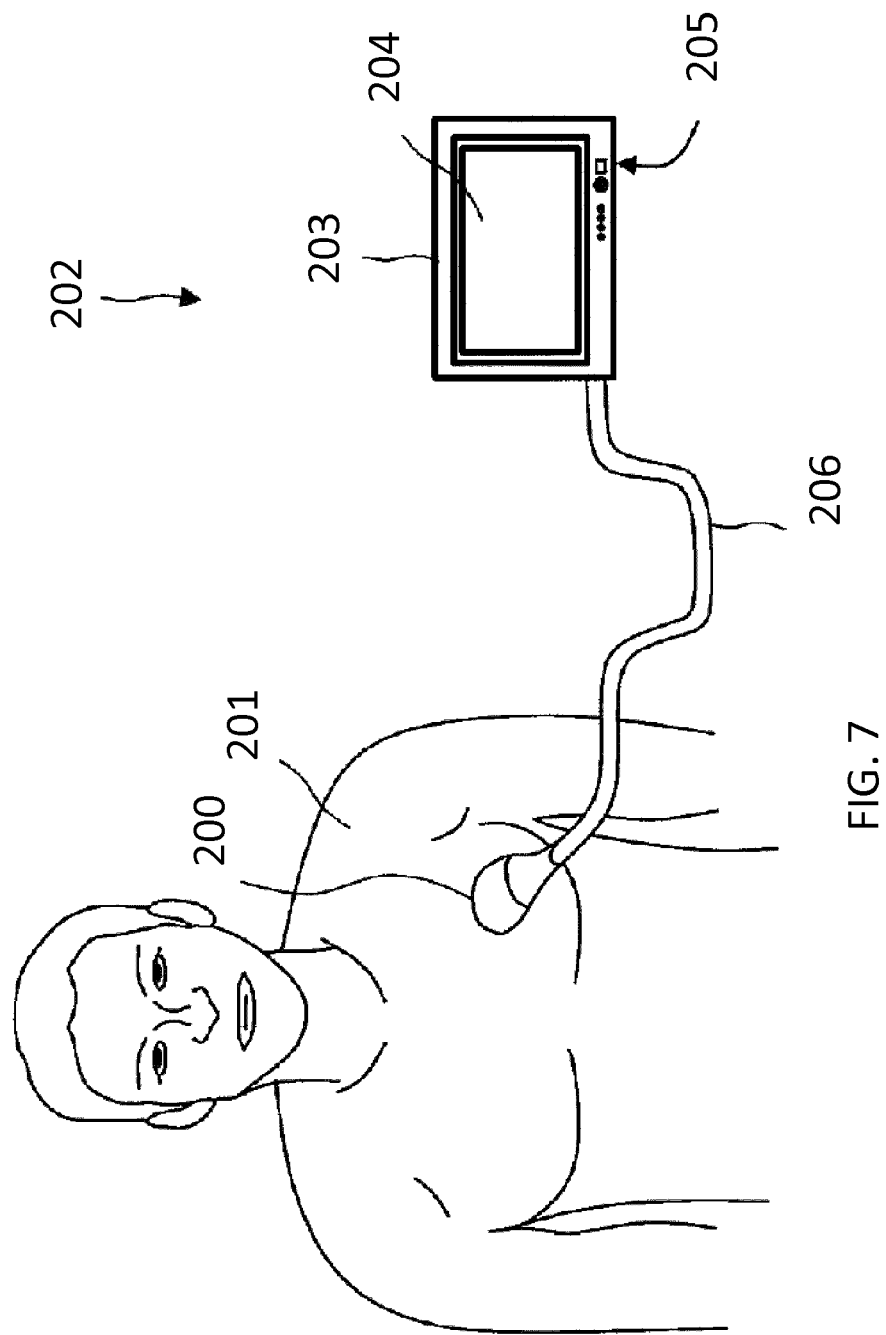
FIG. 7 shows a schematic illustration of an embodiment of an ultrasound imaging system.

FIG. 7 illustrates the principle design of an ultrasonic imaging system 202.

The ultrasound imaging system is generally denoted with reference numeral 202. The ultrasound imaging system 202 is used for scanning an area or volume of the body, e.g. of a patient 201. It is to be understood that the ultrasound system 202 may also be used for scanning other areas or volumes, e.g. body parts of animals or other living beings.

For scanning the patient 201, an ultrasound probe 200 may be provided. In the embodiment shown, the ultrasound probe 200 is connected to a console device 203. The console device 203 is shown in FIG. 7 as a mobile console. This console 203 may, however, also be realized as a stationary device. The console device 203 is connected to the probe 200 via an interface 206 formed in a wired manner. Further, it is contemplated that the console device 203 may also be connected to the probe 200 in a wireless manner, for example using UWB transmission technology. The console device 203 may further comprise an input device 205. The input device may have buttons, a key pad and/or a touchscreen to provide an input mechanism to a user of the ultrasound imaging system 202. Additionally or alternatively, other mechanisms may be present in the input device 205 to enable a user to control the ultrasound imaging system 202.

Further, the console device 203 comprises a display 204 to display display data generated by the ultrasound imaging system 10 to the user. By this, the volume within the patient 201 that is scanned via the ultrasound probe 200 can be viewed on the console device 203 by the user of the ultrasound system 200.

The ultrasound probe 200 comprises the CMUT transducer array constructed in accordance with the present invention.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A capacitive micro-machined ultrasound transducer (CMUT) cell comprising:
   a cell floor having a first electrode;
   a cell membrane having a second electrode which opposes the first electrode and vibrates during transmission or reception of acoustic energy; and
   an acoustic lens, overlaying the cell membrane, and having an inner surface opposing the cell membrane and an outer surface; and
   wherein the acoustic lens comprises:
      a moisture barrier layer disposed over and contacting the cell membrane,
      wherein the moisture barrier layer is formed as part of the acoustic lens such that an inner surface of the moisture barrier layer is the inner surface of the acoustic lens;
      a first layer of polydimethylsiloxane (PDMS) disposed over and in contact with the moisture barrier layer;
      a single layer of conductive material disposed over and in contact with the first layer of PDMS, the single layer of conductive material configured to act as a radio frequency shield;
      a second layer of PDMS disposed over and in contact with the single layer of conductive material; and
      a layer of biocompatible material disposed over the second layer of PDMS.

2. The CMUT cell according to claim 1, wherein the acoustic lens further comprises at least one of the following layers:
   (i) a layer of adhesive material;
   (ii) an acoustic wave focusing layer; or
   (iii) a durable exterior layer located as the outer surface.

3. The CMUT cell according to claim 2, wherein the acoustic lens further comprises at least one layer of liquid.

4. The CMUT cell according to claim 1, wherein the first and second layers of PDMS are cured or uncured PDMS.

5. The CMUT cell according to claim 1, wherein the acoustic lens further comprises at least one layer of gel.

6. The CMUT cell according to claim 5, wherein the at least one layer of gel is a silicone gel.

7. The CMUT cell according to claim 1, wherein the moisture barrier layer comprises at least one of: polyimide, mylar, polyethylene or parylene.

8. The CMUT cell according to claim 1 further comprising a durable exterior layer located as the outer surface that is made from one of polyimide or polyethylene.

9. The CMUT cell according to claim 1, wherein the acoustic lens comprises a layer of adhesive material that comprises silicon oxide.

10. The CMUT cell according to claim 9, further comprising a layer of adhesive disposed between and in contact with the cell membrane and the moisture barrier layer.

11. An ultrasonic imaging system comprising the CMUT cell according to claim 1.

12. The CMUT cell according to claim 1, wherein the acoustic lens further comprises a layer made of polyether block amide (PEBAX) located at the outer surface.

13. The CMUT cell according to claim 1, wherein the second electrode is embedded within the cell membrane such that the second electrode is spaced from the acoustic lens by at least a portion of the cell membrane.

14. The CMUT cell according to claim 1, wherein the layer of biocompatible material comprises the outer surface of the acoustic lens.

15. The CMUT cell according to claim 1, wherein the acoustic lens further comprises a layer comprising silicone.

16. A capacitive micro-machined ultrasound transducer (CMUT) cell comprising:
   a cell floor having a first electrode;
   a cell membrane having a second electrode which opposes the first electrode and vibrates during transmission or reception of acoustic energy; and
   an acoustic lens, overlaying the cell membrane, and having an inner surface opposing the cell membrane and an outer surface; and
   wherein the acoustic lens comprises:
      a moisture barrier layer disposed over and contacting the cell membrane,
      wherein the moisture barrier layer is formed as part of the acoustic lens such that an inner surface of the moisture barrier layer is the inner surface of the acoustic lens;
      a first layer of a lens material disposed over and in contact with the moisture barrier layer, wherein the lens material has an acoustic loss per millimeter for acoustic energy passing therethrough of less than 1.5 dB for energy of an acoustic frequency of 2 MHz, and wherein the lens material has an acoustic propagation velocity for acoustic energy passing therethrough which of between 0.5 and 2.5 mm/microsecond;
      a single layer of conductive material disposed over and in contact with the first layer of lens material, the single layer of conductive material configured to act as a radio frequency shield;
      a second layer of the lens material disposed over and in contact with the single layer of conductive material; and
      a layer of biocompatible material disposed over the second layer of lens material.

17. The CMUT cell according to claim 16, wherein the lens material comprises at least one of polybudatiene, polyether block amide (PEBAX), polydimethylsiloxane (PDMS) or buthyl rubber.

18. The CMUT cell according to claim 16, wherein the biocompatible material comprises at least one of polyimide, polyethylene, or PEBAX.

19. The CMUT cell according to claim 16, wherein the moisture barrier layer comprises at least one of: polyimide, mylar, polyethylene or parylene.

20. The CMUT cell according to claim 16, wherein the conductive material comprises a metal.

\* \* \* \* \*